United States Patent
Acosta

(10) Patent No.: US 8,163,540 B2
(45) Date of Patent: *Apr. 24, 2012

(54) FILTERED PETRI DISH

(76) Inventor: Carlo Acosta, Bellerose, NY (US)

( * ) Notice: Subject to any disclaimer, the term of this patent is extended or adjusted under 35 U.S.C. 154(b) by 710 days.

This patent is subject to a terminal disclaimer.

(21) Appl. No.: 11/425,765

(22) Filed: Jul. 18, 2008

(65) Prior Publication Data
US 2010/0015694 A1    Jan. 21, 2010

(51) Int. Cl.
C12M 1/12 (2006.01)
C12M 1/22 (2006.01)
C12M 3/00 (2006.01)
C12M 1/34 (2006.01)
C12M 1/00 (2006.01)

(52) U.S. Cl. ............ 435/297.5; 435/305.2; 435/305.3; 435/305.4; 435/288.3; 435/307.1

(58) Field of Classification Search ............ 435/297.5, 435/305.2, 305.3, 305.4, 288.3, 307.1
See application file for complete search history.

(56) References Cited

U.S. PATENT DOCUMENTS

| | | | |
|---|---|---|---|
| 4,435,508 A * | 3/1984 | Gabridge | 435/297.5 |
| 4,801,548 A * | 1/1989 | Takakura et al. | 435/288.4 |
| 5,817,509 A | 10/1998 | Stevens et al. | |
| 5,863,792 A * | 1/1999 | Tyndorf et al. | 435/297.5 |
| 5,882,922 A * | 3/1999 | Tyndorf et al. | 435/305.3 |
| 6,521,451 B2 | 2/2003 | Potter | |
| 7,713,734 B2 * | 5/2010 | Ghosh et al. | 435/305.4 |
| 2004/0146965 A1 | 7/2004 | Brayton | |
| 2007/0148649 A1 * | 6/2007 | Shigesada et al. | 435/6 |

FOREIGN PATENT DOCUMENTS

WO    WO 2005/037983    *  4/2005

* cited by examiner

Primary Examiner — Nathan Bowers
Assistant Examiner — Lydia Edwards
(74) Attorney, Agent, or Firm — Jones Day

(57) ABSTRACT

A petri dish includes a cover and base, the cover having at least one circular opening in the top of the cover. A number of securing members are connected to the underside of the cover around the opening to secure at least one filter under the opening, the filter(s) being used to prevent any contaminants from the air from entering the petri dish. A guard member such as a plastic disc is disposed under the filter(s) to prevent any oil in the base of the petri dish from contaminating the filter(s). A sealing member is provided on a peripheral edge of the base to seal the petri dish when the petri dish is closed.

6 Claims, 2 Drawing Sheets

FILTERED PETRI DISH

FIELD OF THE INVENTION

The present invention is directed to a petri dish. In particular, the present invention is directed to a petri dish that includes an air filter(s), thereby minimizing contamination of a culture within the petri dish.

BACKGROUND OF THE INVENTION

Petri dishes are known in the art, the first petri dish having been invented by the German bacteriologist Mr. Julius Richard Petri in 1877. In general, the petri dish is a shallow glass or plastic cylindrical dish that biologist use to culture microbes. Usually, the petri dish is partially filled with warm liquid agar along with a particular mix of nutrients, salts and amino acids, and optionally, antibiotics, that match the metabolic needs of the microbe being studied. After the agar solidifies, the petri dish is ready to receive the microbe to be studied.

When a petri dish is being used, i.e., when it contains an active tissue culture, it is often stored in an incubator with other petri dishes. Typically, due to space limitations within the incubator, the petri dishes are stacked. In a typical laboratory environment, the applicable air filters are installed or connected to the incubator or other holding unit that contains multiple petri dishes, each of which can be contaminated if the air within the holding unit is contaminated. Controlling contamination within the significantly larger holding unit is potentially compromised whenever the holding unit is opened to access any of the multiple petri dishes in the holding unit. Under typical laboratory conditions, users access the holding unit a number of times in a specified time period. For example, if there are 30 petri dishes in a holding unit, a laboratory technician may open the holding unit each time he or she needs to access a single petri dish, exposing the air in the holding unit to the large air volume in the room outside the holding unit. Even though the holding unit may itself be filtered, each time the unit is opened, the elements in the air within the unit are potentially compromised by the room air. Although the holding unit ultimately then filters the new room air, during the time it takes the unit to re-filter the air, the culture in the petri dish is exposed to a less than optimal environment. The petri dish needs access to air and obtains such air in the space(s) where the top and bottom of the petri dish, or other pieces of the dish, come together when the dish is closed. By using a filtered petri dish, the possibility of contamination is limited to the times when the specific petri dish is opened to access its contents. The inventor of the present invention has achieved significantly greater productivity with the filtered petri dish design. Therefore, there is clearly a need for a petri dish having a filter incorporated therein for filtering air entering the petri dish.

SUMMARY OF THE INVENTION

An embodiment of the present invention is directed to an apparatus for culturing cells. The apparatus includes a cover member having a top part with a vertical wall extending downwardly from the periphery of the top part, a center area of the top part having at least one generally circular-shaped opening. The apparatus also includes a plurality of securing members, each of said securing members having a vertical leg and a horizontal leg. The vertical leg includes a first end connected to an underside of the cover member around the generally circular-shaped hole. Moreover, the vertical leg further includes a second end having a means for attaching an article. The horizontal leg of the securing member extends from the vertical leg inwardly. The apparatus also includes a base member having a bottom part with a vertical wall extending upwardly from the periphery of the bottom part, the vertical wall including a peripheral edge at an upper end.

Another embodiment of the present invention is directed to an apparatus for culturing cells. The apparatus includes a cover member having a top part with a vertical wall extending downwardly from a periphery of the top part, a center area of the top part having at least one generally circular-shaped opening. The apparatus also includes a plurality of securing members, each of the securing members having a vertical leg and a horizontal leg. The vertical leg of the apparatus includes a first end connected to an underside of the cover member around the generally circular-shaped hole. The vertical leg further includes a second end having a means for attaching an article, and the horizontal leg extends from the vertical leg inwardly. The apparatus also includes at least one filter member having an upper surface and lower surface, the lower surface of the at least one filter member being situated on the horizontal legs of the plurality of securing members. A guard member of the apparatus is connected to the means for attaching, and a base member of the apparatus has a bottom part with a vertical wall extending upwardly from the periphery of the bottom part, the vertical wall including a peripheral edge at an upper end.

Other objects, features and advantages of the embodiments of the present invention will be apparent from the following detailed disclosure, taken in conjunction with the accompanying sheets of drawings, wherein like reference numerals refer to like parts, in which:

DESCRIPTION OF THE DRAWINGS

FIG. 2 also shows, in dotted lines, a cross-sectional view of an assembled filtered petri dish stacked on top of another filtered petri dish, in solid lines.

DETAILED DESCRIPTION

Figure 1:
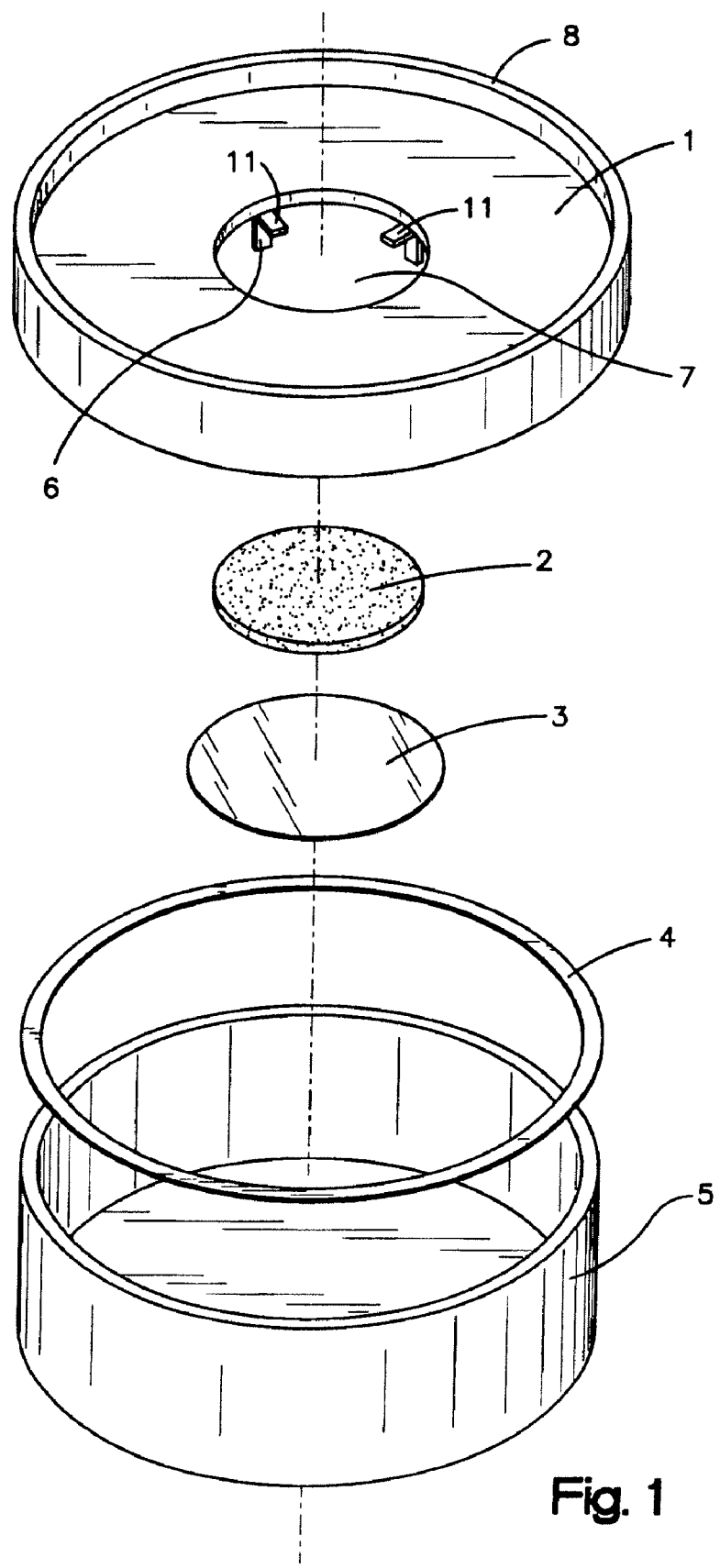
FIG. 1 shows an exploded top perspective view of a filtered petri dish constructed in accordance with an embodiment of the present invention.
Figure 2:
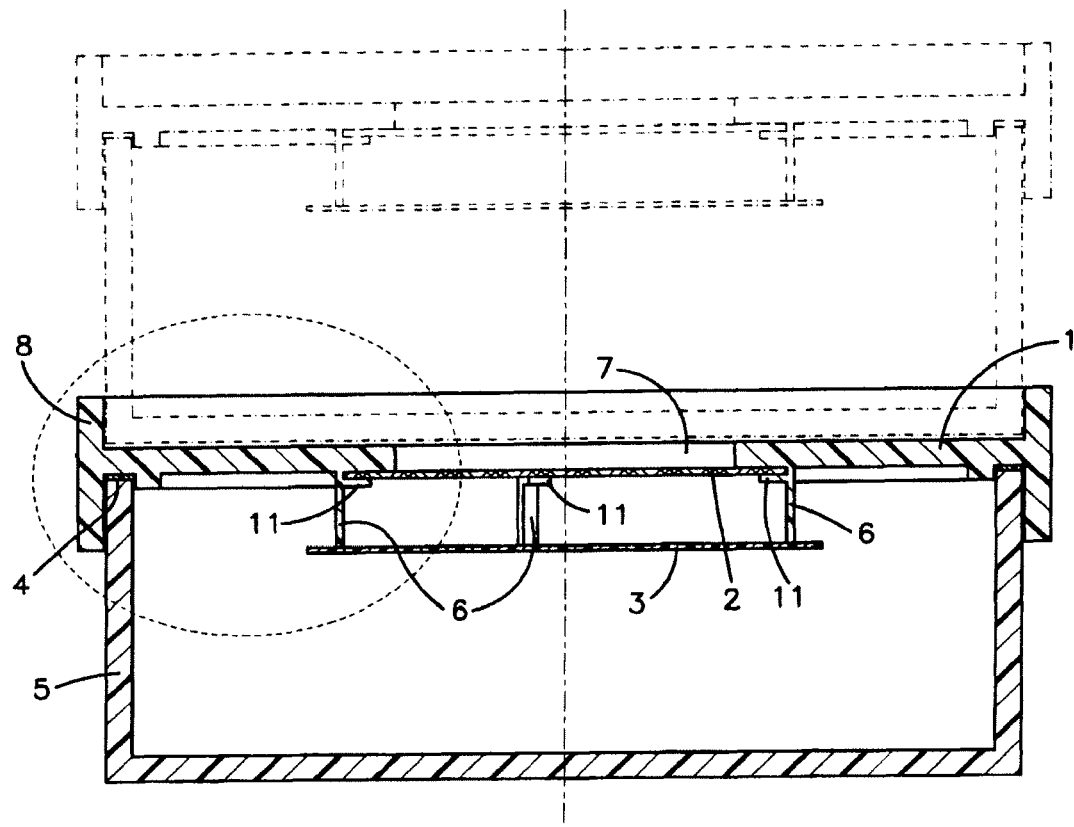
FIG. 2 shows a cross-sectional view of an assembled filtered petri dish constructed in accordance with an embodiment of the present invention.
Figure 3:
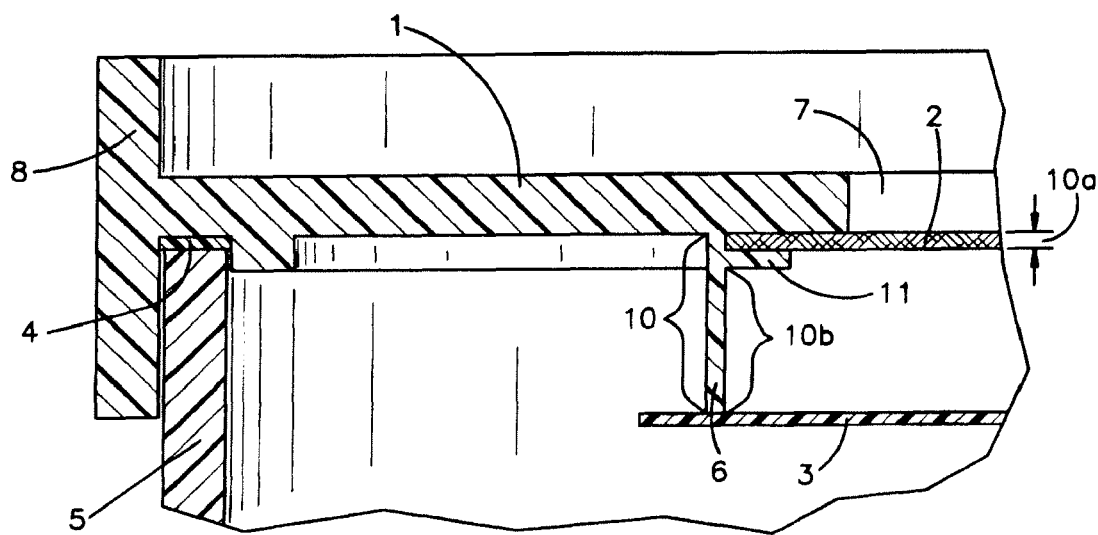
FIG. 3 shows a close-up view of the circled section of FIG. 2.

An embodiment of the present invention is shown in FIGS. 1-3. Referring to FIG. 1, the features of a preferred embodiment of the present invention include, among other things, a cover 1, filter 2, disc 3, seal member 4, base 5 and securing rings 6.

A person of ordinary skill in the art will understand that the petri dish can be of any size, shape, or configuration to accommodate the cells, tissues, etc., that are desired to be cultured, and can be made of any suitable material. However, for purposes of this description, a preferred and known in the art shape of the petri dish is round. The size of the dish is preferably about[1] 35 mm in diameter and preferably about 12 mm in height. The cover 1 of the petri dish preferably has about a 2 mm ridge 8 preferably along its perimeter to facilitate the stacking and venting of the dishes, and to keep the dishes together when a stack of dishes is either placed into, or removed from, the incubator. A person of ordinary skill in the art will understand that the ridge 8 is preferably continuous around the perimeter of the cover 1 as shown in FIG. 1.

However, the ridge 8 may be broken (non-continuous) and have different configurations on its top surface in order to facilitate the stacking and venting of the petri dishes. FIG. 2 shows one petri dish (in dotted lines) stacked on another petri dish (in solid lines). FIG. 2 also shows that the diameter of the bottom, horizontal surface of the base 5 is less than the diameter of the ridge 8, which allows each disc to be easily stacked on top of each other, the ridge being constructed to hold the upper dish in place when stacked. In addition, although not shown in the figures, the bottom, horizontal surface of the base 5 may include legs, ridges or other means of raising the base 5 off the cover 1 allowing, e.g., air to enter a lower dish if dishes are stacked together. Similarly, the top cover 1 may include bumps, ridges or other means of preventing the base from resting on a top surface of the cover 1 thereby allowing air to enter a lower dish if dishes are stacked together.

[1] The word "about," as used in the specification and claims mean "approximately."

The cover 1 of the petri dish preferably has one circular hole 7 in the center. There is no preferred diameter of the hole 7, i.e., it should be large enough to ensure an adequate flow of air into the petri dish. Moreover, although the preferred shape of the hole 7 is circular as shown in FIG. 1, a person of ordinary skill in the art will understand that the hole 7 may comprise a number of shapes including, e.g., a square, rectangular, or related shape. In addition, although not preferred, the cover 1 may include a number of smaller diameter holes throughout the cover, in any number of arrangements and shapes, as long as the holes allow a sufficient amount of air into the petri dish.

A circular 0.2 micron microbiological filter is preferably inserted immediately beneath the hole 7, on the underside of the cover 1, on the interior side of upper section 10a, and is supported by horizontal legs 11 (both 10a and 11 being shown in FIG. 3 and described below). The filter 2 is preferably impregnated with an active charcoal. However, a person of ordinary skill in the art will understand that other filters[2] can be used instead of a filter 2 utilizing an active charcoal ingredient. Moreover, although FIGS. 1-3 only show the petri dish using one filter, the petri dish for this embodiment of the present invention may use one or more filters at the same time. For example, two filters may be used at one time, one filter may be used to filter organic compounds such as volatile organic compounds and a second filter may be used to filter microbiological compounds. In addition, the thickness of the filter 2 may vary depending on the laboratory conditions. For example, a thicker filter 2 may be used in a more contaminated environment; conversely, a thinner filter 2 may be used in a less contaminated environment. The preferred embodiment shows the filter 2 disposed on the underside of the cover 1. The location of the filter 2 on the underside of the cover is particularly desirable when, e.g., several petri dishes are stacked together because the horizontal surface of the base 5 of the upper petri dish does not rest directly on the filter of the lower petri dish thereby decreasing the likelihood that the filter will be damaged in use. When a filter or permeable membrane 40 as described in U.S. Pat. No. 6,521,451 is used on the top, horizontal surface of the cover, the membrane may be damaged when one or more petri dishes are stacked together because the horizontal surface of the base 5 of the upper petri dish will rest directly on the membrane of the lower petri dish. However, a person of ordinary skill in the art will understand that the filter 2 may be situated on top of the cover 1, over hole 7, and may be secured to the cover 1 by any number of ways understood by someone of ordinary skill in the art including, e.g., a velcro strip on an outer ring of the filter 2 that adheres to a corresponding ring on the cover 1.

[2] known or unknown in the art at the time of filing this application

The filter 2 preferably extends beyond the hole 7 and is secured to the underside of the cover 1 by preferably four to six generally L-shaped plastic rings 6 spaced at regular intervals just outside the hole 7. The rings 6 are connected to the underside of the cover 1 of the petri dish and extend underneath the filter 2 to hold the filter 2 in place. As shown more clearly in FIG. 3, the generally L-shaped rings 6 include a vertical leg 10 and horizontal leg 11, the vertical leg 10 preferably having a greater length than the horizontal leg 11, with the vertical leg having an upper section 10a and lower section 10b, the upper section 10a of the vertical leg 10 being connected to the underside of the cover. This connection may be made when the cover 1 is fabricated in, e.g., a molding process that includes a mold for the cover, the desired dimensions and the rings 6 extending downward from the underside of the cover. The cover 1 and rings 6 may also be made separately and secured together in a manner understood by someone of ordinary skill in the art, e.g., if the rings 6 are plastic, by applying an adhesive at the connection point. A person of ordinary skill in the art will also understand that the filter 2 may be secured any number of ways to the underside of the cover including, e.g., a velcro strip on an outer ring of the filter 2 that adheres to a corresponding ring on the underside of the cover 1. In the claims, for example, the recitation "means for securing" may include the rings 6, velcro design described above or other equivalent structural features known or unknown in the art at the time of filing this application.

A clear, circular, thin plastic disc 3 is preferably inserted underneath the filter 2 to separate the filter 2 from the culture in the bottom of the base 5 which, often oily in nature, can clog the filter 2. The disc 3 may have different shapes, e.g., square, rectangle, etc., as long as the shape preferably covers the filter 2 and prevents the filter 2 from clogging. The disc 3 preferably does not touch the filter 2, the distance between the disc 3 and the filter 2 preferably being about 2 mm. The distance between the filter 2 and the top of the disc 3 is maintained by the length of the lower section 10b of vertical leg 10 (shown in FIG. 3); the distance may vary depending on laboratory conditions and the user's desire. A plastic post (not shown) is preferably attached to the bottom of each ring 6. The post protrudes downward and is attached to the disc 3 (the post is just one example of the "means for attaching" the disc 3 to the ring 6 as such recitation is used in the claims; other equivalent structural means known or unknown to a person of ordinary skill in the art at the time of filing this application are available to attach the disc 3 to the ring 6). The culture in the base 5 of the dish can thus touch the bottom of the disc 3; however, the disc stops the culture from moving upwards to clog the filter 2. The filter 2 at times may become contaminated either by the contaminated air flowing through the filter 2 (but not into the base 5) or by oil somehow flowing past or splattering in the base 5 thereby contaminating the filter 2. When the filter 2 does get contaminated, it can be easily removed and a new clean filter 2 may be installed accordingly.

The base 5 preferably has eight circular wells for holding tissue cultures. The wells are spaced at equidistant points in a circle, with no well beneath the filter 2. Each well is about 2 mm high and about 3 mm in diameter. The distance from the edge of the bottom of the base 5 to the well is about 3 mm. For identification purposes, each well is numbered, with the number preferably just outside each well. The wells to be used for holding the tissue culture for prolonged periods, as opposed to washing the culture, are preferably marked with a colored square around the well.

The base 5 includes a horizontal surface having an interior and exterior side. The base 5 also includes a cylindrical section having a vertical wall extending from a periphery of the horizontal surface of the base 5. A typical known in the art configuration of the base 5 is shown in FIGS. 1 and 2. The vertical wall of the base 5 has an upper peripheral edge that mates with a corresponding section on the underside of the cover 1 to close the dish, as best shown in FIGS. 2 and 3. A circular gasket 4 may be placed around the upper peripheral edge for sealing the dish when the dish is closed, the circular gasket or other sealing means being referred to in the claims as "the sealing member" or "means for sealing." In a preferred embodiment, the upper peripheral edge includes an inner ring that is about 1 mm deep and about 1 mm wide. The ring is preferably filled with clay, rubber or other non-toxic sealing culture. When the dish is closed, i.e., when the cover 1 is placed on top of the base 5, the clay secures the cover 1 to the base 5 so that the dish 3 is airtight, with air entering the dish only through the filter 2.

An example of an embodiment of the filtered petri dish of the present invention in use will be discussed below. The culture is placed in the base 5 by removing the cover 1 of the dish to enable the laboratory technician to place the culture in the base 5 of the dish. While the culture is in the base 5, the laboratory technician will observe and work with the culture either by examining the culture from outside the dish, e.g., by using a microscope with the dish closed, or by opening the dish when physical access to the culture is needed. The environment within the dish is potentially compromised only when the technician needs to place the culture in the base 5, work with the culture while in the base 5, or remove the culture from the base 5. At all other times, the dish's environment is secure, with air entering the dish only through the attached filter 2. By using a filtered petri dish, when a laboratory technician opens the incubator in which multiple petri dishes are stored, the individual dish is not potentially compromised when the technician removes another dish.

The specification was provided in this application to describe to someone of ordinary skill in the art how to make and use embodiments of the present invention directed to the filtered petri dish. The specification is not intended, and should not be interpreted, as limiting in any way the scope of the claims. The word "preferred" as used in this specification is used to describe the preferred or best mode of using the aspects of the present invention, not to limit the aspects of the present invention to those preferences.

It will be understood that modifications and variations may be effected without departing from the scope of the novel concepts of the embodiments of the present invention, but it is understood that this application is to be limited only by the scope of the appended claims.

I claim:

1. An apparatus for culturing cells comprising:
   a cover member having a top part with a vertical wall extending downwardly from a periphery of the top part, a center area of the top part having one generally circular-shaped opening;
   a plurality of securing members, each of said securing members having a vertical leg and a horizontal leg,
   wherein the vertical leg includes a first end connected to an underside of said cover member around the perimeter of the circular-shaped opening,
   wherein the vertical leg further includes a second end having a means for attaching, and
   wherein the horizontal leg extends from the vertical leg inwardly;
   at least one filter member having an upper surface and lower surface, the lower surface of said at least one filter member being situated on the horizontal legs of said plurality of securing members;
   a guard member connected to the means for attaching,
   wherein the filter member and the guard member are separate members and are separated by a vertical distance; and
   a base member having a bottom part with a vertical wall extending upwardly from the periphery of the bottom part, the vertical wall including a peripheral edge at an upper end.

2. The apparatus according to claim 1, further comprising a seal member situated on the peripheral edge.

3. The apparatus according to claim 1, further comprising a ridge extending vertically upward from the top part of said cover member, said ridge having substantially the same diameter as the vertical wall extending vertically downward from the top part of said cover member.

4. The apparatus according to claim 3, wherein said ridge is capable of being continuous or non-continuous.

5. An apparatus for culturing cells comprising:
   a cover member having a top part with a vertical wall extending downwardly from a periphery of the top part, a center area of the top part having one generally circular-shaped opening;
   a plurality of ring members for securing at least one filter member to the underside of said cover member around the perimeter of the opening, each ring member including a vertical leg and a horizontal leg extending inwardly from the vertical leg, wherein the vertical leg includes a first end attachable to the underside of said cover member and a second end;
   means for attaching a guard member to the second end of the vertical leg, wherein the guard member and filter member are separated by a vertical distance; and
   a base member having a bottom part with a vertical wall extending upwardly from the periphery of the bottom part, the vertical wall including a peripheral edge at an upper end.

6. An apparatus for culturing cells comprising:
   a cover member having a top part with a vertical wall extending downwardly from a periphery of the top part, a center area of the top part having one generally circular-shaped opening;
   at least one filter member;
   a plurality of ring members for securing at least one filter member to the underside of said cover member around the perimeter of the circular-shaped opening, each ring member including a vertical leg and a horizontal leg extending inwardly from the vertical leg wherein the vertical leg includes a first end attachable to the underside of said cover member and a second end;
   means for attaching an article to the second end of the vertical leg:
   a guard member situated under said at least one filter member, separated by a vertical distance; and
   a base member having a bottom part with a vertical wall extending upwardly from the periphery of the bottom part, the vertical wall including a peripheral edge at an upper end.

* * * * *